United States Patent [19]

Früngel

[11] 4,432,645
[45] Feb. 21, 1984

[54] FORWARD-SCATTER VISIBILITY METER

[76] Inventor: Frank Früngel, Im Glockenacker 2, 8053 Zürich, Switzerland

[21] Appl. No.: 196,144

[22] Filed: Oct. 10, 1980

[51] Int. Cl.³ .................................................. G01N 21/49
[52] U.S. Cl. .................................. 356/338; 350/582; 350/588; 356/341
[58] Field of Search ............... 356/338, 341; 250/574; 350/61, 66, 67

[56] References Cited

U.S. PATENT DOCUMENTS

| | | | |
|---|---|---|---|
| 2,399,971 | 5/1946 | Wolfe | 350/66 |
| 3,510,666 | 5/1970 | Topol | 250/574 |
| 3,653,768 | 4/1972 | Menke | 250/574 X |
| 3,671,128 | 6/1972 | Radke et al. | 250/574 X |
| 3,672,775 | 6/1972 | Fruengel | 250/574 X |
| 3,901,588 | 8/1975 | Longhenry | 356/338 X |
| 3,985,453 | 10/1976 | Nakano et al. | 250/574 X |
| 4,099,178 | 7/1978 | Ranney et al. | 250/574 X |

FOREIGN PATENT DOCUMENTS

| | | | |
|---|---|---|---|
| 52-35687 | 3/1977 | Japan | 356/338 |
| 55-36785 | 3/1980 | Japan | 250/574 |
| 566013 | 8/1975 | Switzerland | |
| 1400311 | 7/1975 | United Kingdom | |

OTHER PUBLICATIONS

Winstanley, "Automatic Fog Warning", *Systems Technology* No. 22, pp. 26–31, Oct. 1975.

*Primary Examiner*—William L. Sikes
*Assistant Examiner*—Matthew W. Koren
*Attorney, Agent, or Firm*—Michael J. Striker

[57] ABSTRACT

Two embodiments of the visibility meter are disclosed. In the first embodiment, light transmitted from the light transmitter and light received by the light receiver is propagated in a conical beam. The beams are so oriented that they include an obtuse angle. In the first embodiment, a partition blocks all direct transmission of light from the light transmitter to the light receiver. In the second embodiment, direct transmission of light from the light transmitter to the light receiver takes place through the partition, but is limited to a predetermined level.

15 Claims, 4 Drawing Figures

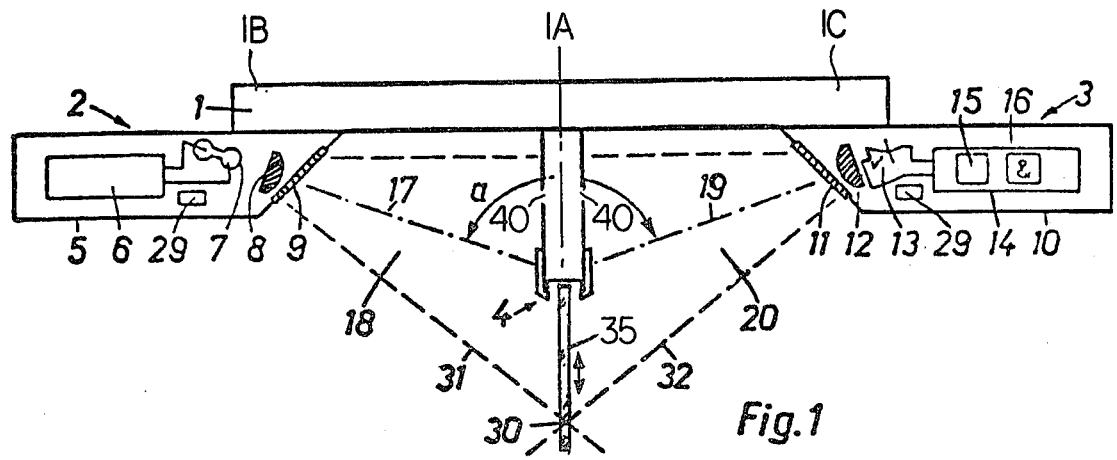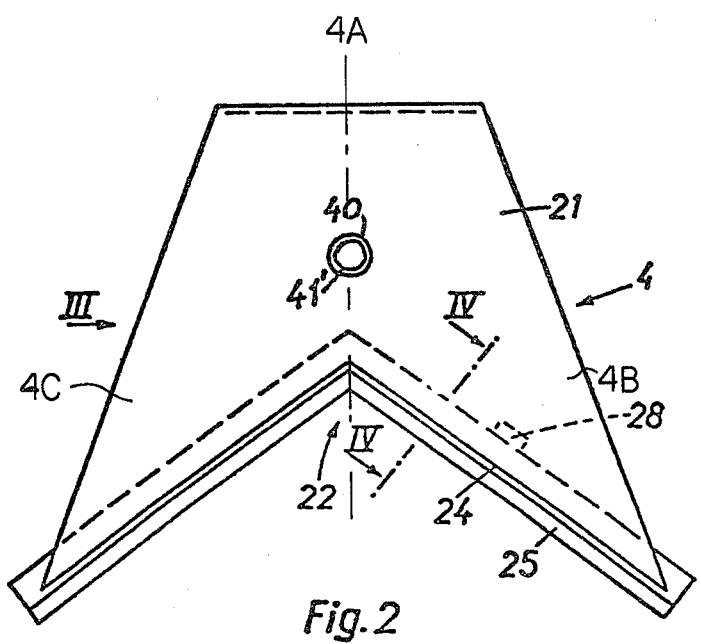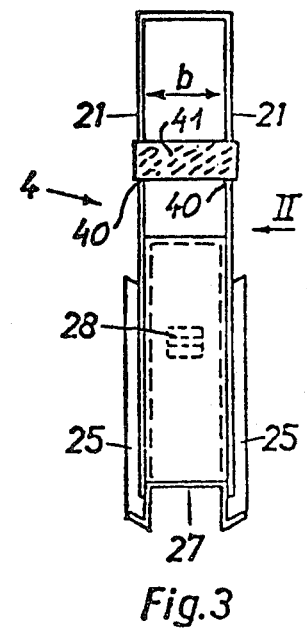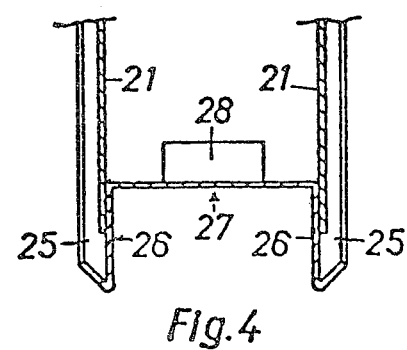
Fig.1
Fig.2
Fig.3
Fig.4

FORWARD-SCATTER VISIBILITY METER

BACKGROUND OF THE INVENTION

1. Field of the Invention

This invention pertains to visibility meters, such as are used in metereology, aeronautics and in automotive traffic-control systems as a warning device detecting the presence of fog.

2. Description of the Prior Art

Prior-art visibility meters have proved to be subject to malfunction as a result of weather conditions and environmental disturbances. In prior-art devices, maintenance is required in order to clean the exterior surfaces of the optical systems in the light transmitter and the light receiver. If, for example, dust particles land upon either the light transmitter or the light receiver, readings derived from the visibility meter will be inaccurate. This can lead to severe problems, especially in the event that the visibility meter is installed at, e.g., an airport where accurate visibility measurements are essential.

Therefore, it would be advantageous to provide a visibility meter which would require only minimal maintenance and which would be less sensitive to the influences of weather conditions and environmental disturbances, such as the presence of insects and the like.

SUMMARY OF THE INVENTION

These objects, along with others which will become apparent hereinafter, are achieved in this invention primarily by a novel orientation of the light transmitter and the light receiver with respect to each other. While in prior-art devices the light transmitter and the light receiver lie along a horizontal line which is interrupted by a diaphragm or partition, this invention improves upon such an arrangement by orienting the light transmitter and the light receiver with respect to each other such that the axes of light transmission and light reception include an oblique angle which is bisected by a partition. In this fashion, it is more difficult for dust particles and other undesirable substances to adhere to either the light transmitter or the light receiver and thereby impair measurement accuracy.

In one embodiment of the invention, the partition blocks all direct transmission of light from the light transmitter to the light receiver. In this embodiment, light received by the light receiver must of necessity be reflected off moisture particles in the air. Therefore, an accurate visibility reading is taken.

In another embodiment of this invention, the partition is perforated by a perforation which precisely limits direct transmission of light from the light transmitter to the light transmitter to a predetermined level. In this embodiment, it is necessary to recalibrate the light receiver in order to achieve the necessary measurement accuracy. However, as will be seen hereinafter, the effects of light transmission to the receiver are additive, so that after satisfactory recalibration the receiver will operate as accurately as in the first embodiment described above.

Of particular interest in this invention are advantageous features which may be built into the partition itself. Advantageously, the partition can be manufactured not as a simple planar sheet but rather as a relatively thick structure with a predetermined width. As will be seen hereinafter, this construction helps to insure measurement accuracy even in the event that raindrops adhere to the bottom edge of the partition. Also advantageously, the partition is divided at its bottom to form two like downwardly and outwardly extendings wings which are symmetrical about its centerline. As a result of this construction, raindrops tend to drip off rain gutters which may advantageously be located along the bottom edge, in order to further increase measurement accuracy. Other advantageous features which may be incorporated into the partition are a heater which heats the partition sufficiently to prevent spiders from forming webs upon it and water-repellant and insect-killing coatings on the partition that prevent the accumulation of raindrops and insects upon it.

Because the atmospheric region in which measurement takes place is below the invention, no heating of this region takes place, and thermals therein, which reduce accuracy, are reduced. By choosing an appropriate oblique angle, the invention can be made vertically compact. It therefore need not be mounted on an overly long post above the ground. Moreover, noise at the light receiver is reduced by its inclination from the prior-art horizontal orientation.

The novel features which are considered as characteristic for the invention are set forth in particular in the appended claims. The invention itself, however, both as to its construction and its method of operation, together with additional objects and advantages thereof, will best be understood from the following description of specific embodiments when read in connection with the accomanying drawing.

BRIEF DESCRIPTION OF THE DRAWINGS

FIG. 1 is a schematic side view of the invention;

FIG. 2 is a front view of the partition utilized in this invention;

FIG. 3 is a cross-sectional view of the partition taken along its centerline; and FIG. 4 is a view of the partition taken along line IV—IV as is shown in FIG. 2.

DETAILED DESCRIPTION OF PREFERRED EMBODIMENTS

Referring first to FIG. 1, it can be seen that an elongated support 1 has a center 1A, a first end 1B and a second end 1C. A light transmitter generally indicated by reference numeral 2 is located beneath support 1 at first end 1B, while a light receiver generally indicated by reference numeral 3 is located beneath support 1 at second end 1C.

Light transmitter 2 is contained within housing 5, and contains a power supply 6 which energizes and deenergizes a flash lamp 7, which may advantageously be a gas discharge flash lamp. Light from flash lamp 7 passes through an optical system which is schematically represented as lens 8, and thence passes through window 9 and out of light transmitter 2. Window 9 and housing 5 are both air-tight, and an adsorbent bag or capsule 29 which may contain, e.g., silica gel is placed within housing 5 so as to prevent moisture from condensing within housing 5 at low temperature, preventing growth of bacteria and fungus.

Light receiver 3 is contained within housing 10, and receives light through window 11 which is attached to housing 10. Window 11 and housing 10 are air-tight, and light receiver 3 likewise contains an adsorbent bag or capsule 29. After passing through window 11, light received by light receiver 3 then passes through an optical system schematically represented by lens 12, which focuses the light onto a photosensitive element 13, which may advantageously be a photodiode. Photosensitive element 13 is connected to electronic circuitry schematically indicated by reference numeral 14. Circuitry 4 includes an electrical filter 15 which calibrates the response of light receiver 3 so that it corresponds with a frequency band in which light received by light receiver 3 carries a maximum energy. Circuitry 14 further includes an electrical switch 16, which may advantageously be an AND-gate. Electrical switch 16 switches light receiver 3 off inbetween flashes of flash lamp 7 in a fashion such as that disclosed in Swiss Pat. No. 566 013.

To further reduce growth of bacteria and/or fungus in light transmitter 2 or light receiver 3, windows 9 and 11 can be made of either barite or quartz.

Light projected by light transmitter 2 is projected through window 9 in a generally conical beam 18 along a first axis 17. In a similar fashion, light received by light receiver 3 is received from a generally conical beam 20 along second axis 19. Angle a included between first axis 17 and second axis 19 is oblique, since axis 17 extends downwardly and towards center 1A and second axis 19 extends upwardly and away from center 1A.

A partition generally indicated by reference numeral 4 is attached to center 1A of support 1 and extends vertically downwardly therefrom intermediate light transmitter 2 and light receiver 3.

Partition 4, as can be seen in more detail in FIG. 2, has a centerline 4A and is divided at its bottom to form two like wings 4B and 4C which extend outwardly from centerline 4A and are symmetrical about it. Thus, bottom edge 24 is peaked at centerline 4A and extends downwardly and outwardly therefrom in the shape of an inverted V.

Partition 4 is formed by two parallel outer walls 21 which are held apart from each other by a distance b. Each outer wall 21 supports a rain gutter 25 which extends along bottom edge 24 and which is either riveted or screwed to that one of the outer walls 21 to which it is attached. Rain gutter 25 extends upwardly and outwardly from its corresponding outer wall 21, so that drops of water on wall 21 will be prevented in the main from hanging on bottom edge 24 on either side of partition 4. Advantageously, each outer wall 21 may be coated with a water-repellant coating such as Teflon and/or an insecticide.

In a first embodiment of the invention, outer walls 21 are unperforated and thereby completely block all light incident upon them. Partition 4 is so shaped that all direct transmission of light from light transmitter 2 to light receiver 3 is blocked by partition 4. However, as can be seen from FIG. 1, conical beam 18 and conical beam 20 intersect each other below partition 4, so that point 30 is located below partition 4 along centerline 4A thereof, and is formed at the intersection of line 31 (which indicates the lowest line along beam 18) and line 32 (which indicates the lowest line on beam 20). Hence, in this first embodiment of the invention, light in beam 18 can only reach light receiver 3 by reflecting off moisture particles in the atmosphere which are located below and around the bottom of partition 4. Hence, the output from photosensitive element 13 accurately reflects visibility, because in this first embodiment of the invention the only way that any light will be received by light receiver 3 is if such light reflects off atmospheric moisture particles such as are caused by clouds or fog.

Thickness b of partition 4 serves to reduce sensitivity of light receiver 3 to the effects of water droplets. In the event that water droplets adhere to the right-hand rain gutter 25 as viewed in FIG. 1, such water droplets will be in the shade of the left-hand rain gutter 25 and will therefore have no effect in reflecting light to light receiver 3. Moreover, water droplets hanging from the left-hand rain gutter 25 as viewed in FIG. 1 will tend to have only a minimal effect on reflection of light into light receiver 3, since partition 4 is comparatively thick and the water droplets are relatively small. It will be appreciated by those skilled in the art that in the event water droplets were permitted to reflect light from light source 7 into light receiver 3, that light receiver 3 would have an output indicating a lesser visibility than that which actually existed, since light receiver 3 would interpret light incident upon it as being reflected by moisture particles in the atmosphere rather than by water droplets on partition 4. Advantageously, formation of such water droplets is further impeded by coating outer walls 21 with a water-repellant coating, such as has been described above. Insects may be prevented from perching on partition 4 by coating outer walls 21 with an insecticide.

Outer walls 21 are held apart from each other by distance b by a support plate 27, which takes the form of an inverted V, as does bottom edge 24. Support plate 27 supports a thermostatically controlled heater 28. It has been determined that spiders will not spin webs which would adhere to partition 4 if the partition is maintained at a temperature of between 50° C. and 60° C. Heater 28 serves the function of maintaining partition 4 at this temperature, in order to keep spiders and their webs away from partition 4. This is of importance to the practice of this invention in that under proper climatic conditions, a spider web (when attached to partition 4) can cause the visibility as measured by light receiver 3 to be understated by approximately 1 kilometer. As in the case of water droplets, a spider web attached to partition 4 will increase the amount of light received by light receiver 3, and will therefore tend to cause visibility to be understated. In winter, partition 4 need not be heated to such high temperatures, and it is therefore advantageous if heater 28 is made adjustable, so as to maintain partition 4 at a temperature which is only slightly above 0° C. in order to prevent any buildup of snow or ice on partition 4. It will be appreciated by those skilled in the art that heater 28 will not tend to heat the air below partition 4, so that heater 28 does not cause false readings by light receiver 3 to occur by developing thermals below partition 4.

In use, support 1 is suspended sufficiently high that the visibility meter will be located above any level to which snow may rise, in order to prevent snow from interfering with visibility measurement accuracy. Furthermore, the entire device may be surrounded by a wire screen having a mesh size of, e.g., one centimeter. This screen will prevent spiders from being blown by the wind onto partition 4. Moreover, the screen prevents insects, and particularly butterflies, from landing on partition 4. However, flow of air is not adversely influenced so that visibility measurements can take place without reduction in accuracy. Of course, for visibility meters which are intended for use in nautical applications, and which are mounted on bouys, the screen will not be necessary.

In order to reduce the likelihood of vandalism, the visibility meter will preferably be painted a drab color in order to avoid attracting the attention of vandals. For visibility meters which are installed at fixed locations above the ground, the ground will advantageously be coated with a unitary covering such as concrete, asphalt, plastic, or metal plating in order to prevent plant growth from arising in crevices and thereby growing into the open bottom of the device. Advantageously, whatever covering is utilized on the ground will be colored white or at least will have a light hue, in order to prevent the covering from heating up as a result of incident sunshine and a corresponding heating up of the atmosphere underneath partition 4, which is undesirable as was described above.

Inasmuch as human beings do not see radiation which is located in the infrared portion of the spectrum, it is disadvantageous for light receiver 3 to respond to infrared light. In order to prevent such response, and in order to prevent light from conventional light sources and electrical components from disturbing measurement accuracy by virtue of the infrared radiation which they generate, it is advantageous to provide either light transmitter 2 or light receiver 3 or both with means for preventing response to infrared radiation. Preferably, this can be done by providing either window 9 or window 11 with an infrared filter, or by making either windows 9 and 11 or lenses 8 and 12 of infrared-absorbing material. Preferably, at least light receiver 3 will be protected in this fashion.

Inasmuch as visibility only changes slowly, it is unnecessary to continuously monitor visibility of the atmosphere. Moreover, non-continuous measurement of visibility will reduce power consumption and will prolong the useful life of the device, and will particularly increase the lifespan of flash lamp 7. Therefore, it is advantageous to provide the device with a control system (not shown) which repeatedly operates the visibility meter for short periods. Furthermore, the visibility meter can be provided with a memory (not shown) in which readings of visibility measurements may be stored. If visibility, as measured, changes during two successive short periods of operation, an indicating system (not shown) may be activated in order to inform a user that visibility has changed. Momentary events such as the presence of foreign matter blown into the visibility meter by the wind or the presence of a butterfly can thus be neglected, since they are transitory and will not continuously affect visibility measurement.

Alternatively, and in the event that the invention is utilized as a warning device to inform motorists of the presence of fog, the invention can be provided with an indicating system (not shown) which informs a user when visibility is less than a predetermined value. Advantageously, this value can be varied between 140 meters during the daytime and 90 meters at night. This may be accomplished by, e.g., a clock (not shown) which varies the predetermined value in accordance with times of day and night, or by a light sensor such as a photocell which varies the predetermined value in accordance with ambient light intensity.

In order to test the device, a light-transmissive plate 35 may be introduced below partition 4, in order to insure that light will be received by light receiver 3. This not only serves to indicate that the device is operating, but also serves to calibrate the device in the event that the light-transmissive characteristics of the plate are accurately known in advance. Thus, such a light-transmissive plate can be used to calibrate the visibility meter. If desired, a plate-moving mechanism, preferred actuated by a magnet, can be used to automatically move the plate (not shown) below partition 4 in order to verify proper operation and in order to allow calibration to take place, and the plate can then be moved away from partition 4 by the plate-moving mechanism when such calibration has been finished.

As was stated above, the first embodiment of the invention blocks all direct transmission of light from the light transmitter to the light receiver. However, it is possible to build the invention in such a fashion that it monitors its own operation and thereby provides an indication when a failure or a miscalibration takes place. It is known that the effects of light received by light receiver 3 have a cumulative, additive effect. Therefore, in a second embodiment of the invention partition 4 is perforated by a perforation shown by reference numeral 40 in the drawing. This perforation permits direct transmission of light from the light transmitter to the light receiver, but limits such transmission to a predetermined level. This in turn, causes light receiver 3 to continuously indicate a lower visibility than actually exists. However, since such direct transmission of light is held to this predetermined level, it is possible to recalibrate light receiver 3 in order to correct for the direct transmission. For example, let it be assumed that a visibility of 120 meters produced a 0.5 mA current through photosensitive element 13. Furthermore, let it be assumed that by choosing perforation 40 to be of a suitably small size, a visibility of 800 meters can be simulated by direct transmission of light through perforation 40, creating a 0.1 mA current through photosensitive element 13. Under these conditions, a current of 0.6 mA will be present through photosensitive element 13 when actual visibility is 120 meters.

It can be seen that a current of 0.6 mA would be ordinarilyy interpreted to correspond with a visibility of less than 120 meters, but that by a suitable recalibration of light receiver 3 accurate measurements can be obtained by virtue of the additive effects of light incident upon photosensitive element 13 upon current flowing through it. Additionally, since perforation 40 will always permit enough light to be transmitted directly from light transmitter 2 to light receiver 3 to cause a current of 1 mA to flow through photosensitive element 13, an automatic check on the operability of the invention is provided. If current through photosensitive element 13 ever decreases below 0.1 mA, a user will immediately realize that a malfunction has taken place.

As alternative constructions, it is possible to fill perforation 40 with a plug 41 of a suitably light-transmissive material, or with a suitable light diffuser (not shown). Either of these alternative constructions may be utilized to reduce direct light transmission through partition 4. A suitable material for plug 41 is Teflon. This material is advantageous not only because of its light-transmissive properties, but also because it is a water-repellant substance. Furthermore, a ring 41' may be mounted on each of outer walls 21. This will inhibit formation of water droplets which can vary the predetermined level of light which is transmitted directly through partition 4.

When this second embodiment is utilized, the predetermined level of light which is directly transmitted through partition 4 is empirically set at such a value that the artificially derived visibility resulting therefrom will be higher than any visibility of which accurate measurement is deemed to be of consequence. Thus, for example, in the event that user requirements dictate that it is only necessary to detect whether or not visibility is below e.g. 120 meters, the predetermined level of direct light transmission through partition 4 may be set at, e.g., 800 meters.

It will be understood that each of the elements described above, or two or more together, may also find a useful application in other types of meters differing from the types described above.

While the invention has been described and illustrated as embodied in a forward-scatter visibility meter, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A forward-scatter visibility meter, comprising:
   an elongated support with a center and first and second ends;
   a light transmitter located beneath the support at the first end and directing a generally conical beam of light along a first axis which extends downwardly and towards the center;
   a light receiver located beneath the support at the second end and receiving a generally conical beam of light along a second axis which extends upwardly and away from the center in a manner that the first and second axes are symmetrical about the center of the support and include an obtuse angle;
   a partition attached to the center of the support and extending downwardly therefrom in a manner that all direct transmission of light from the light transmitter to the light receiver is blocked by the partition, said partition having a bottom and a vertical centerline, and being divided at its bottom to form two like downwardly and outwardly extending wings which are symmetrical about the centerline, and wherein each of the wings has a bottom edge and two outside faces, and wherein a rain gutter is located along the bottom edge along each outside face.

2. The visibility meter defined by claim 1, wherein the partition is coated with a water-repellant coating.

3. The visibility meter defined by claim 1, wherein the partition is coated with an insecticide.

4. The visibility meter defined by claim 1, wherein the partition includes a heater heating the partition to a temperature between approximately 50° C. and 60° C.

5. The visibility meter defined by claim 1, wherein the partition is hollow.

6. The visibility meter defined by claim 1, wherein the light transmitter and light receiver contain a moisture adsorbent and are airtight.

7. The visibility meter defined by claim 1, wherein the light transmitter transmits light through a first window, and wherein the light receiver receives light through a second window.

8. The visibility meter defined by claim 7, wherein the first and second windows are made of barite.

9. The visibility meter defined by claim 7, wherein the first and second windows are made of quartz.

10. The visibility meter defined by claim 1, wherein at least the receiver is provided with a means absorbing infrared light received by the receiver.

11. The visibility meter defined by claim 10, wherein the means is an infrared filter.

12. The visibility meter defined by claim 10, wherein the means is an infrared-absorbing lens.

13. The visibility meter defined by claim 1, wherein the light transmitter includes a flash lamp.

14. The visibility meter defined by claim 13, wherein the light receiver includes an electrical filter calibrating response of the light receiver to a frequency band in which light received by the light receiver carries a maximum energy.

15. A forward-scatter visibility meter, comprising:
   an elongated support with a center and first and second ends;
   a light transmitter located beneath the support at the first end and directing a generally conical beam of light along a first axis which extends downwardly and towards the center;
   a light receiver located beneath the support at the second end and receiving a generally conical beam of light along a second axis which extends upwardly and away from the center in a manner that the first and second axes are symmetrical about the center of the support and include an obtuse angle;
   a partition attached to the center of the support and extending downwardly therefrom in a manner that all direct transmission of light from the light transmitter to the light receiver is blocked by the partition; and
   further including a control system, a memory, and an indicating system, wherein the control system repeatedly operates the visibility meter for short periods, wherein the memory stores visibility measurements obtained during such repeated operations, and wherein the indicating system informs a user when a visibility measurement changes during at least two successive short periods.

* * * * *